United States Patent [19]

Ohyama et al.

[11] Patent Number: 5,248,784

[45] Date of Patent: Sep. 28, 1993

[54] 4-CARBONYL-SUBSTITUTED COUMARIN COMPOUND

[75] Inventors: Tsukasa Ohyama; Kazuhiko Murayama; Yoriaki Matsuzaki; Susumu Kasamatsu; Keisuke Takuma; Kimitoshi Kato, all of Fukuoka, Japan

[73] Assignee: Mitsui Toatsu Chemicals, Inc., Tokyo, Japan

[21] Appl. No.: 870,786

[22] Filed: Apr. 16, 1992

Related U.S. Application Data

[63] Continuation of Ser. No. 629,693, Dec. 18, 1990, abandoned.

[30] Foreign Application Priority Data

Dec. 28, 1989 [JP] Japan .................. 1-338282

[51] Int. Cl.$^5$ .................. C07D 403/04; C07D 413/04; C07D 417/04
[52] U.S. Cl. ........................ 548/159; 548/204; 548/217; 548/236; 548/305.1; 549/399
[58] Field of Search ............ 549/399; 548/159, 305.1, 548/204, 217, 236

[56] References Cited

U.S. PATENT DOCUMENTS 4,547,579  10/1985  Möckli .................. 549/280

FOREIGN PATENT DOCUMENTS 137177   4/1985  European Pat. Off. .
8703589  6/1987  World Int. Prop. O. .

OTHER PUBLICATIONS

Winters, Appl. Phys. Letter 25, 723 (1974) Abstract only.
Dyes and Pigments, vol. 1, 1980, pp. 3–15; P. Moeckli: "Preparation of Some New Red Fluorescent 4-Cyanocoumarin Dyes".

*Primary Examiner*—Robert Gerstl
*Attorney, Agent, or Firm*—Burns, Doane, Swecker & Mathis

[57] ABSTRACT

A novel 4-carbonyl-substituted coumarin compound which is substituted with a carbonyl group in the position-4 of a 7-alkylaminocoumarin derivative and has photosensitivity in the visible region.

7 Claims, 2 Drawing Sheets

4-CARBONYL-SUBSTITUTED COUMARIN COMPOUND

This application is a continuation of application Ser. No. 07/629,693, filed Dec. 18, 1990, now abandoned.

BACKGROUND OF THE INVENTION

1) Field of the Invention

The present invention relates to a novel 4-carbonyl-substituted coumarin compound, and more particularly relates to a 4-carbonyl-substituted coumarin compound which provides a novel photosensitizer for use in photosetting resins.

2) Description of the Related Art

In the field of information recording using a photopolymerization reaction, it has recently been investigated to replace conventional recording methods from a film copy through ultraviolet rays with a recording system for directly outputting through laser beams an intact original which is electronically edited with a computer. However, many sources which are generally used today for radiating high output and stable laser beams have a wavelength output in the visible region as observed in argon laser beams. Conventionally used sensitizing agents for ultraviolet rays cannot be employed because of low sensitivity in the visible region. Addition of pyrylium salts or thiapyrylium salts can improve the sensitivity in the visible region. On the other hand, the addition of such salts deteriorates the stability of a photosensitive layer over time. These salts have hence been difficult to use.

Conventionally, 7-alkylaminocoumarin derivatives have a maximum absorption wavelength of from 400 to 450 nm in the case of 4-unsubstituted derivatives. However, many laser beams which are generally used have longer wavelengths than the above range and thus satisfactory sensitivity cannot be obtained in many cases.

For example, 7-diethylamino-3-benzothiazoylcoumarin and 3,3'-carbonylbis(7-diethylaminocoumarin) have a maximum absorption wavelength of about 450 nm, which wavelength is from 30 to 40 nm shorter than 488 nm of argon laser beams. These compounds still have room for improving sensitivity. Since a positive correlation is set up in a certain range between the content of the sensitizer in the resin and the sensitivity obtained, it is desired to form a stable solution of the sensitizer in the resin in the highest concentration within the given range. The above two compounds have poor solubility and lead to a low sensitizer concentration in the resin. Thus the desired sensitivity cannot be obtained.

The maximum absorption wavelength of these compounds can be shifted to a longer wavelength (hereinafter referred to simply as long wave shift) by converting the position-4 to a cyano group. However, solubility in the resin or storage stability are impaired in many cases.

SUMMARY OF THE INVENTION

One object of the invention is to provide a novel 4-carbonyl-substituted coumarin compound.

Another object of the invention is to provide a 4-carbonyl-substituted coumarin compound which is useful as a sensitizer for photosetting resins having improved sensitivity in the visible region.

As a result of carrying out an intensive investigation in order to solve the above problems, the present inventors have found a novel 4-carbonyl-substituted coumarin compound and the present invention has been completed.

An aspect of the present invention is a 4-carbonyl-substituted coumarin compound represented by the formula (I):

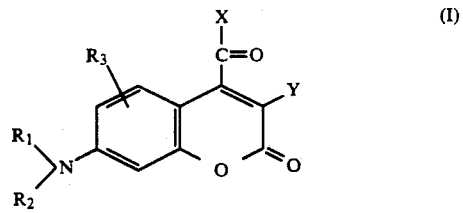

wherein $R_1$ and $R_2$ are the same or a different group selected from a hydrogen atom, alkyl group, alkoxyalkyl group, alkenyl group, hydroxyalkyl group, aralkyl group, aryl group and alkoxycarbonylalkyl group, and may be bonded to each other or with a benzene ring having an amino substituent in the coumaron skeleton to form a ring; $R_3$ is selected from a hydrogen atom, alkyl group, alkoxyalkyl group, hydroxyalkyl group, halogenoalkyl group, hydroxyl, alkoxy group, alkoxyalkoxy group, alkoxycarbonyl group, sulfonic acid group, and a halogen atom; X is selected from a hydrogen atom, alkyl group, cycloalkyl group, alkoxy group, cycloalkoxy group, hydroxyl group, aryl group, alkenyl group, aryloxy group, alkenyloxy group, aralkyl group, aralkyloxy group, alkoxycarbonylalkoxy group, alkylcarbonylalkoxy group and a group represented by the following formula:

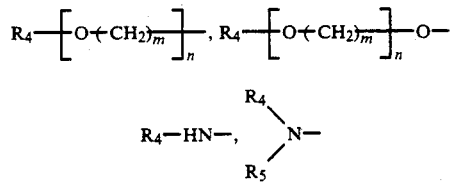

wherein $R_4$ and $R_5$ are selected from a hydrogen atom, alkyl group, hydroxyalkyl group, hydroxyalkoxyalkyl group, alkoxyalkyl group and cycloalkyl group, and m and n are respectively an integer of from 1 to 5; and Y is selected group a hydrogen atom, alkylcarbonyl group, alkoxycarbonyl group, aryl group, arylcarbonyl group, aryloxycarbonyl group, alkoxycarbonylalkylcarbonyl group, alkoxycarbonylalkoxycarbonyl group and a heterocyclic ring.

The compound of the invention is a novel coumarin compound which is useful as a sensitizer. The compound has simultaneously accomplished a long wave shift of the maximum absorption wavelength and high solubility in the resin by introducing a substituted carbonyl group into the position-4 of the coumarin skeleton. The coumarin compound is very useful as a photosetting resin, for example, a photo-polymerizable or photo-crosslinkable compound having at least one ethylenically unsaturated linkage in a molecule and as a compound capable of being applied to a photosetting system using a photo-polymerization initiator. Further, conventional sensitizers cause a large variation in sensitivity depending upon the difference of the coating method. On the other hand, the sensitizer of the invention achieves a stable sensitivity in any coating method and can fully satisfy this requirement.

The compound represented by the formula (I) has never been described in the literature and has been confirmed that the compound is a novel compound.

The 4-carbonyl-substituted coumarin compound of the invention is a novel compound and is very useful as a novel photosensitizer.

Conventionally in the field of information recording using a photopolymerization reaction, a recording system for directly outputting through laser beams provides an intact original which is electronically edited with a computer. However, this system leads to inferior time-dependent stability and low sensitivity of the photosensitive layer and also has problems of solubility in the resin and storage stability of the resultant solution.

On the other hand, a photosensitive film obtained by coating the photosensitive resin composition containing the photosensitizing dye of the invention is excellent in sensitivity and storage stability. Hence, the present invention is very valuable in practical use.

BRIEF DESCRIPTION OF THE DRAWINGS

The drawings illustrate IR absorption spectra of the compounds obtained in the examples of the invention.

DESCRIPTION OF THE PREFERRED EMBODIMENTS

Figure 1:
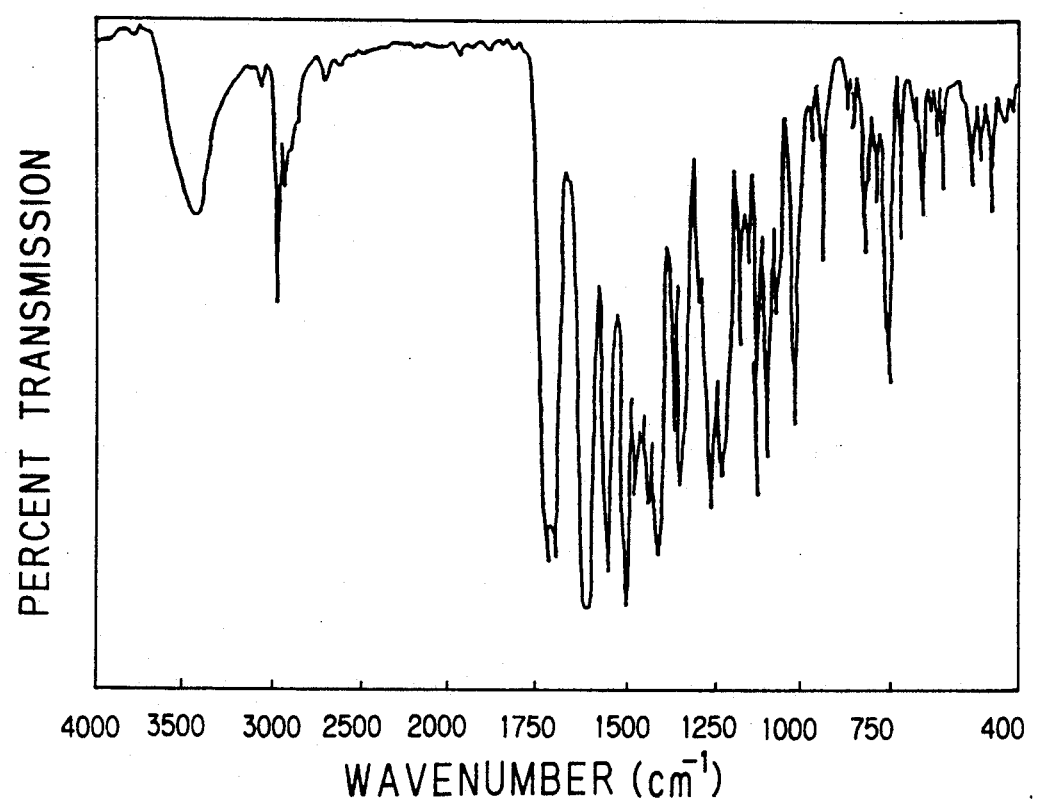
FIG. 1 illustrates IR absorption spectrum of 3-(benzothiazo-2-yl)-4-ethoxycarbonyl-7-diethylaminocoumarin prepared in Example 1.

The present invention will hereinafter be described in detail.

The compound of the invention is a coumarin compound comprising a carbonyl substituent in the position-4 as clearly illustrated by the chemical structure represented by the formula (I):

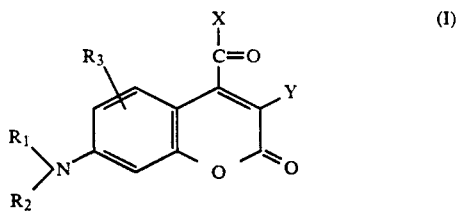

In the formula (I), $R_1$ and $R_2$ are selected from a hydrogen atom, alkyl group, alkoxyalkyl group, alkenyl group, hydroxyalkyl group, aralkyl group, aryl group and alkoxycarbonylalkyl group and may be the same or different. Exemplary $R_1$ and $R_2$ include a hydrogen atom; alkyl group such as methyl, ethyl, n-propyl, isopropyl, n-butyl, isobutyl, sec-butyl, t-butyl, n-pentyl and n-hexyl; alkoxyalkyl group such as methoxymethyl, methoxyethyl, ethoxymethyl, ethoxyethyl, γ-methoxypropyl and γ-ethoxypropyl; alkenyl group such as allyl, γ-butenyl and 2-pentenyl; hydroxyalkyl group such as hydroxymethyl, hydroxyethyl, 2-hydroxypropyl, 3-hydroxypropyl and 2-hydroxybutyl; aralkyl group such as benzyl and phenethyl; aryl group such as phenyl, p-methylphenyl, m-methylphenyl, o-methylphenyl and 2,4-dimethylphenyl; and alkoxycarbonylalkyl group such as methoxycarbonylmethyl, methoxycarbonylethyl, ethoxycarbonylmethyl and ethoxycarbonylethyl.

$R_1$ and $R_2$ may be bonded to each other or with a benzene ring having an amino substituent in the coumarin skeleton to form a ring having the following formulas:

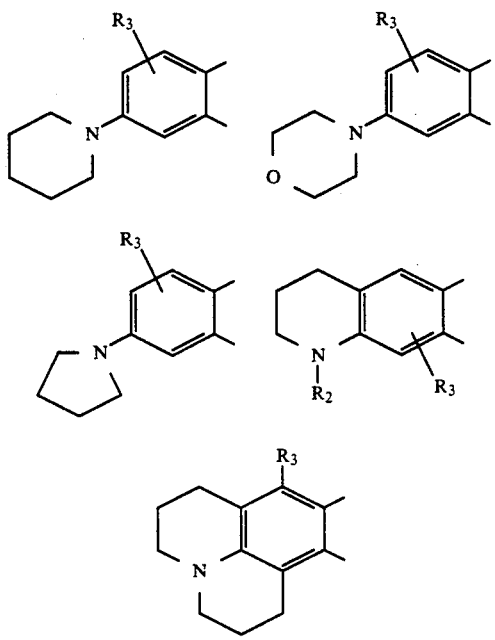

wherein $R_2$ and $R_3$ in these rings are the same as in the formula (I).

In the formula (I), $R_3$ is selected from a hydrogen atom, alkyl group, alkoxyalkyl group, hydroxyalkyl group, halogenoalkyl group, hydroxyl group, alkoxy group, alkoxyalkoxy group, alkoxycarbonyl group, sulfonic acid group and halogen atom. Exemplary $R_3$ includes a hydrogen atom; alkyl group such as methyl, ethyl, n-propyl, isopropyl and n-butyl; alkoxyalkyl group such as methoxymethyl, methoxyethyl, ethoxymethyl and ethoxyethyl; hydroxyalkyl group such as hydroxymethyl, hydroxyethyl, 2-hydroxypropyl and 3-hydroxypropyl; halogenoalkyl group such as chloromethyl, 2-chloroethyl, dichloromethyl and trifluoromethyl; hydroxyl group; alkoxy group such as methoxy, ethoxy, n-propoxy and n-butoxy; alkoxyalkoxy group such a groups methoxymethoxy, methoxyethoxy, ethoxymethoxy, ethoxyethoxy and n-propoxyethoxy; alkoxycarbonyl group such as methoxycarbonyl, ethoxycarbonyl, n-propoxycarbonyl and isopropoxycarbonyl; sulfonic acid group; and halogen atom such as chlorine, fluorine and bromine.

Similarly in the formula (I), X is selected from a hydrogen atom, alkyl group, cycloalkyl group, alkoxy group, cycloalkoxy group, hydroxyl group, aryl group, alkenyl group, aryloxy group, alkenyloxy group, aralkyl group, aralkyloxy group, alkoxycarbonylalkoxy group, alkylcarbonylalkoxy group and a group resprented by the following formula:

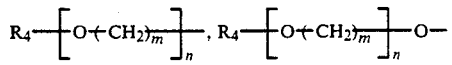

-continued

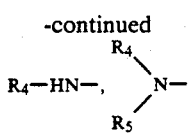

wherein R4 and R5 are selected from a hydrogen atom, alkyl group, hydroxyalkyl group, hydroxyalkoxyalkyl group, alkoxyalkyl group and cycloalkyl group, and m and n are an integer of from 1 to 5. Exemplary X includes a hydrogen atom; alkyl group such as methyl, ethyl, n-propyl, isopropyl, n-butyl, isobutyl, sec-butyl, t-butyl, n-pentyl, n-hexyl, n-heptyl and n-octyl; cycloalkyl group such as cyclopentyl and cyclohexyl; alkoxy group such as methoxy, ethoxy, n-propoxy, isopropoxy, n-butoxy, isobutoxy, sec-butoxy, t-butoxy, n-penoxy, n-hexoxy, n-heptoxy and n-octyloxy; cycloalkoxy group such as cyclopentoxy and cyclohexoxy; hydroxyl group; aryl group such as phenyl, p-methylphenyl, m-methylphenyl and o-methylphenyl; alkenyl group such as 2-butenyl and 2-pentenyl; aryloxy group such as phenoxy, p-methylphenoxy, m-methylphenoxy, o-methylphenoxy, 2,4-dimethylphenoxy, 2,6-dimethylphenoxy, 2,4,6-trimethylphenoxy and 4-phenylphenoxy; alkenyloxy group such as propenoxy and butenoxy; aralkyl group such as benzyl and phenethyl; aralkyloxy group such as benzyloxy, methylbenzyloxy and phenethyloxy; alkoxycarbonylalkoxy group such as methoxycarbonylmethoxy, ethoxycarbonylmethoxy, n-propoxycarbonylmethoxy and iso-propoxycarbonylmethoxy; polyether group such as hydroxyethyl, hydroxyethoxyethyl, hydroxyethoxyethoxyethyl, ethoxyethoxyethyl, hydroxyethoxy, hydroxyethoxyethoxy, hydroxypropoxypropoxy and hydroxyethoxyethoxyethoxy; amino; monoalkylamino group such as methylamino, ethylamino, n-propylamino, n-butylamino, n-pentylamino, n-hexylamino, and n-octylamino; dialkylamino group such as dimethylamino, diethylamino, dipropylamino, dibutylamino, dipentylamino, dihexylamino and dioctylamino; mono(hydroxyalkyl)amino group such as hydroxyethylamino, 2-hydroxypropylamino and 3-hydroxypropylamino; di(hydroxyalkyl)amino group such as di(hydroxyethyl)amino, di(2-hydroxypropyl)amino and di(3-hydroxypropyl)amino; mono(hydroxyalkoxyalkyl)amino group such as hydroxyethoxyethylamino, hydroxypropoxyethylamino and hydroxypropoxypropylamino; di(hydroxyalkoxyalkyl)amino group such as di(hydroxyethoxyethyl)amino, di(hydroxypropoxyethyl)-amino and di(hydroxypropoxypropyl)amino; mono(alkoxyalkyl)amino group such as methoxymethylamino, methoxyethylamino, ethoxymethylamino, ethoxyethylamino and propoxyethylamino; di(alkoxyalkyl)amino group such as di(methoxymethyl)amino, di(methoxyethyl)amino, di(ethoxymethyl)amino, di(ethoxyethyl)amino and di(-propoxyethyl)amino; and cycloalkylamino group such as cyclopentylamino and cyclohexylamino.

Further in the formula (I), Y is selected from a hydrogen atom, alkylcarbonyl group, alkoxycarbonyl group, aryl group, arylcarbonyl group, aryloxycarbonyl group, alkoxycarbonylalkylcarbonyl group, alkoxycarbonylalkoxycarbonyl group and a heterocyclic ring.

Exemplary Y includes a hydrogen atom; alkylcarbonyl group such as methylcarbonyl, ethylcarbonyl, n-propylcarbonyl and n-butylcarbonyl; alkoxycarbonyl group such as methoxycarbonyl, ethoxycarbonyl, n-propoxycarbonyl and n-butoxycarbonyl; aryl group such as phenyl, p-methylphenyl, m-methylphenyl and o-methylphenyl; arylcarbonyl group such as benzoyl, p-methylbenzoyl, m-methylbenzoyl and o-methylbenzoyl; aryloxycarbonyl group such as phenoxycarbonyl, p-methylphenoxycarbonyl, m-methylphenoxycarbonyl and o-methylphenoxycarbonyl; alkoxycarbonylalkylcarbonyl group such as methoxycarbonylmethylcarbonyl and ethoxycarbonylmethylcarbonyl; alkoxycarbonylalkoxycarbonyl group such as methoxycarbonylmethoxycarbonyl and ethoxycarbonylmethoxycarbonyl; or a heterocyclic ring represented by the following formulas:

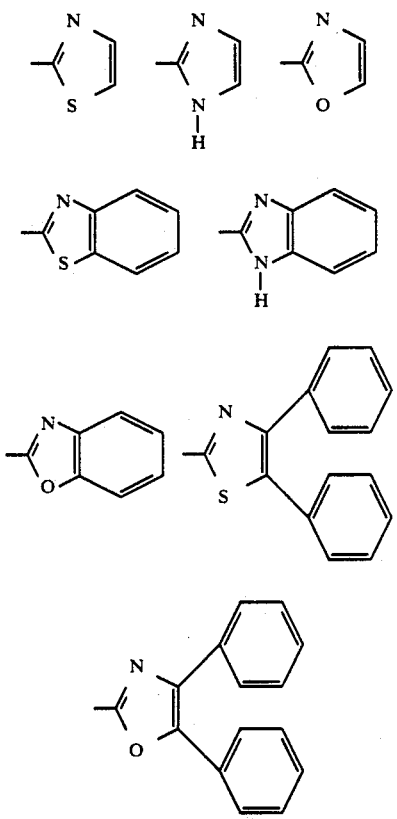

The coumarin compound of the invention can be prepared, for example, by the following reaction.

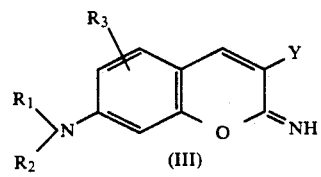

(III)

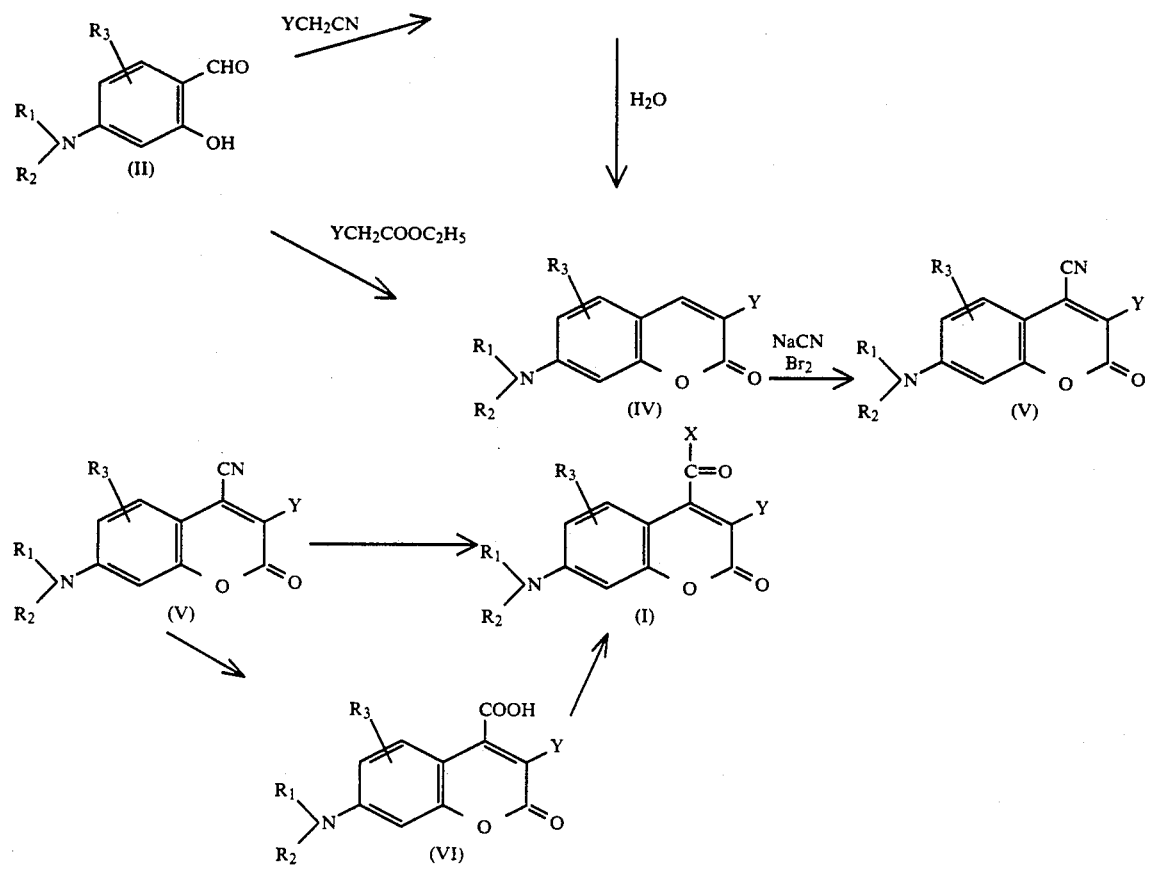

The raw material 4-amino substituted salicylaldehyde (II) is mixed with a cyanomethyl derivative in a ratio of 1:1 in a polar solvent, for example, methanol, ethanol, N,N-dimethylformamide (hereinafter abbreviated as DMF) and dimethyl sulfoxide. To the mixture obtained, a weak base is added as a catalyst in an amount of about one tenth. A preferred weak base is an amine such as piperidine, pyrrolidine, pyridine and aniline. The mixture is reacted at 0° to 80° C. for 1 to 12 hours to obtain compound (III). Compound (III) is boiled for 2 to 6 hours in 5 to 20 times the amount of dilute hydrochloric acid having a concentration of 1 to 5% by weight to give compound (IV). Alternatively, the compound (IV) can be directly obtained without passing through the compound (III) by using an alkoxycarbonylmethyl derivative in place of the cyanomethyl derivative and reacting under the same conditions as above.

Conversion of the compound (IV) to a cyano derivative is carried out according to the method described in Dyes and Pigments, vol 1, page 3–15(1980) the contents of which are incorporated by reference. The compound (IV) is reacted with NaCN in DMF and then oxidized with bromine to obtain the cyano derivative (V).

The cyano derivative (V) can be converted to the novel compound (I) by the following various methods. The cyano group is hydrolyzed by heating at 70° to 100° C. in 50 to 80% by weight of sulfuric acid to give a carboxylic acid derivative (VI). The carboxylic acid derivative (VI) is reacted with alcohols, amines, halogenated alkyls, various acylates or phenols. The reaction is carried out after converting to an acid chloride by reaction with a chlorinating agent or conducted by heating in the presence or absence of an acid catalyst and dehydrating agent. In another method, the compound (I) can be directly obtained by dropwise adding concentrated sulfuric acid to an alcohol solution containing about equimolar amounts of the cyano derivative (V) and water and thereafter heating to 50° to 100° C. A carbon atom can also be introduced directly into the carbonyl group by reacting the cyano group with a Grignard's reagent such as BrMgX.

The present invention will hereinafter be described in detail by way of examples. In the examples, part means part by weight and % means % by weight.

EXAMPLE 1

To a mixture of 20 parts of 4-diethylaminosalicylaldehyde and 18 parts of 2-ethyoxycarbonylmethylbenzothiazol, 1 part of piperidine was added and reacted for 12 hours in ethanol as a solvent. The reaction mixture was filtered and the crystal obtained was washed well with ethanol and dried to obtain 32 parts of 3-(benzothiazo-2-yl)-7-diethylaminocoumarin.

According to the method described in [Dyes and Pigments, vol 1, page 3–15(1980)], 10 parts of the compound was suspended in 50 parts of DMF and 9 parts of a 30% aqueous NaCN solution was dropwise added to the suspension at room temperature. After reacting the mixture for an hour, 5 parts of bromine was dropwise added at 0° to 10° C. and stirred for 2 hours. The reaction mixture was filtered, washed well with water and dried to obtain 3-(benzothiazo-2-yl)-4-cyano-7-diethylaminocoumarin.

Further, 9 parts of the above cyano derivative were reacted with 21.6 parts of 98% sulfuric acid in 100 parts of ethanol at 80° C. for 3 hours, allowed to cool, and poured into 300 parts of water and neutralized.

The precipitated crystal was filtered, washed well with water and dried to obtain 7 parts of 3-(benzothiazo-2-yl)-4-ethoxycarbonyl-7-diethylaminocoumarin.

Melting point; 155°-157° C.

Electron spectrum; Maximum absorption [λmax] 470 nm (in acetone)

Elemental analysis ($C_{23}H_{22}N_2O_4S$):

|  | C | H | N |
|---|---|---|---|
| Calculated (%) | 65.40 | 5.21 | 6.64 |
| Found (%) | 65.31 | 5.33 | 6.69 |

NMR Spectrum (or/ppm) in DMSO-H$_6$: 1.19(t, 6H), 1.35(t, 3H), 3.52(q, 4H), 4.55(q, 2H), 6.65–8.15(m, 7H)

IR Absorption spectrum (KBr tablet): Illustrated in FIG. 1.

A photo-sensitive liquid was prepared by mixing 5 parts of the above coumarin compound, 100 parts of polyvinyl pyrrolidone as a binder polymer, 100 parts of pentaerythritol triacrylate, 4 parts of 3,3',4,4'-tetra(t-butylperoxycarbonyl)benzophenone and 1000 parts of methoxyethanol. The liquid thus obtained was coated on a copper laminate with a spinner.

In the next step, the photosensitive layer obtained was irradiated with a xenon lamp or argon laser. The resin was quickly cured.

EXAMPLE 2

To a mixture of 20 parts 4-diethylaminosalicylaldehyde and 17.5 parts of cyanomethylbenzothiazol, 1 part of piperidine was added and reacted in N,N-diethylformamide as a solvent for 8 hours at room temperature. The reaction mixture was filtered, and the crystal obtained was washed well with ethanol and dried to obtain 28 parts of 3-(benzothiazo-2-yl)-7-diethylamincoumarin-2-imine. The compound was boiled for 8 hours in 400 parts of 2% aqueous hydrochloric acid to obtain 26 parts of 3-(benzothiazo-2-yl)-7-diethylaminocoumarin-2-imine. The compound thus obtained was converted to the cyano derivative by the same procedures as described in Example 1, and 9 parts of the cyano derivative was hydrolyzed at 100° C. for 8 hours in a 70% aqueous sulfuric acid solution to obtain 8.5 parts of 3-(benzothiazo-2-yl)-7-diethylaminocoumarin-4-carboxylic acid.

The carboxylic acid derivative of coumarin obtained was reacted with 4 parts of dicyclohexylcarboimide for an hour at room temperature in 100 parts of dehydrated tetrahydrofuran. Thereafter 4.8 parts of isopropyl alcohol were added dropwise at 10° C. over 30 minutes and reacted for 3 hours at the same temperature to obtain 6.3 parts of 3-(benzothiazo-2-yl)-4-isopropoxycarbonyl-7-diethylaminocoumarin.

Melting point: 196°~198° C.

Electron spectrum: Absorption maximum [λmax] 470 nm (in acetone)

Elemental analysis ($C_{22}H_{24}N_2O_4S$)

|  | C | H | N |
|---|---|---|---|
| Calculated (%) | 66.06 | 5.50 | 6.42 |
| Found (%) | 66.12 | 5.61 | 6.33 |

NMR Spectrum (δ/ppm) in DMSO-H$_6$: 1.19(t,6H), 1.39(t,6H), 3.52(q,4H), 5.45(Sep. 1H), 6.65~8.15(m,7H)

Figure 2:
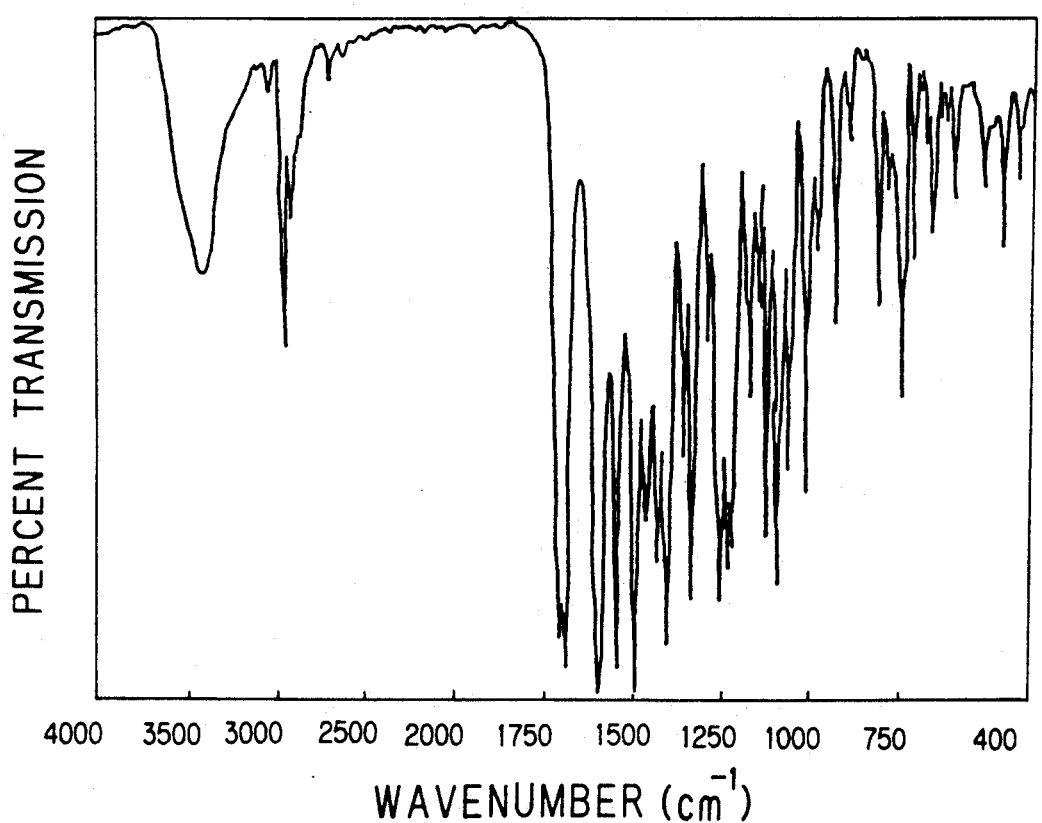
FIG. 2 illustrates IR absorption spectrum of 3-(benzothiazo-2-yl)-4-isopropoxycarbonyl-7-diethylaminocoumarin in Example 2.

IR Absorpotion spectrum (KBr tablet): Illustrated in FIG. 2.

A photosensitive liquid was prepared from the above coumarin compound by carrying out the same procedures as described in Example 1. Thereafter a photosensitive layer was formed by using the liquid thus obtained and irradiated with the xenon lamp and the argon laser. The resin was quickly cured.

EXAMPLE 3

The same procedures as described in Example 1 were carried out except that 100 parts of diethylene glycol was used in place of ethanol in ester synthesis.

The amount of 3-(Benzothiazo-2-yl)-4-hydroxyethoxyethoxycarbonyl-7-diethylaminocoumarin thus obtained was 5 parts.

Melting point: 145°~146° C.

Electron spectrum: Maximum absorption [λmax] 472 nm (in acetone)

Elemental analysis ($C_{25}H_{26}N_2O_6S$)

|  | C | H | N |
|---|---|---|---|
| Calculated (%) | 62.24 | 5.39 | 5.81 |
| Found (%) | 62.21 | 5.45 | 5.72 |

NMR Spectrum (≡/ppm) in DMSO-d$_6$: 1.18(t, 6H), 3.43(t, 4H), 2.52(q, 4H), 3.76(t, 2H), 4.22(t, 2H), 4.63(t, 2H), 6.65~8.22(m, 7H)

Figure 3:
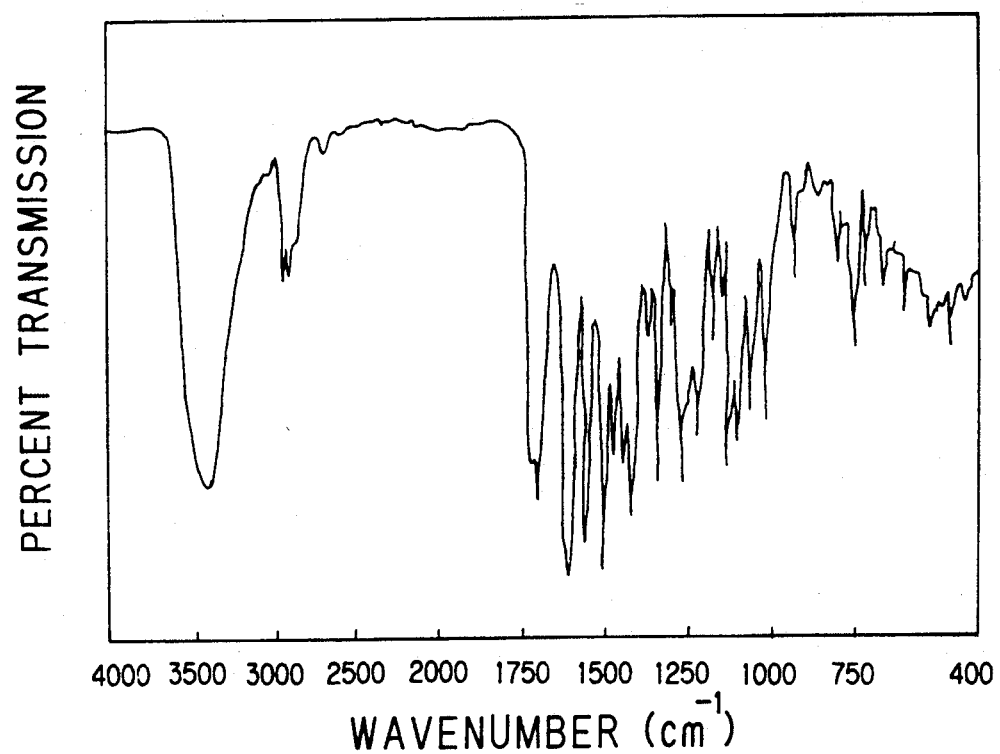
FIG. 3 illustrates IR absorption spectrum of 3-(benzothiazo-2-yl)-4-hydroxyethoxyethoxycarbonyl-7-diethylaminocoumarin prepared in Example 3.

IR Absorption spectrum (KBr tablet): Illustrated in FIG. 3.

EXAMPLES 4–27

The compounds illustrated in Table 1 were prepared according to the method described in Example 1.

Photosensitive liquids having the same compositions as described in Example 1 were prepared by using the coumarin compounds obtained above. Photosensitive layers were formed by carrying out the same procedures as described in Example 1 and irradiated with the xenon lamp and the argon laser. The resins of the photosensitive layers were quickly cured.

TABLE 1

[Structure: coumarin derivative with COX and Y substituents on the vinyl group, and NR₁R₂ on the aromatic ring]

| Example No. | R₁ | R₂ | X | Y | mp (°C.) | | C | H | N |
|---|---|---|---|---|---|---|---|---|---|
| 4 | C₂H₅ | C₂H₅ | OC₄H₉ | benzothiazol-2-yl | 175~176 | (Calc.) | 67.67 | 5.78 | 6.22 |
| | | | | | | (Found) | 66.51 | 5.82 | 6.29 |
| 5 | " | " | OCH₂–C₆H₅ | " | 203~204 | (Calc.) | 69.47 | 4.96 | 5.79 |
| | | | | | | (Found) | 69.66 | 4.90 | 5.77 |
| 6 | " | " | O–C₆H₅ | " | 215~217 | (Calc.) | 68.94 | 4.68 | 5.96 |
| | | | | | | (Found) | 68.98 | 4.54 | 6.05 |
| 7 | " | " | O–(2-CH₃-C₆H₄) | " | 198~199 | (Calc.) | 69.42 | 4.96 | 5.79 |
| | | | | | | (Found) | 69.55 | 5.02 | 5.81 |
| 8 | " | " | OC₂H₄OC₂H₅ | " | 162~163 | (Calc.) | 64.38 | 5.58 | 6.01 |
| | | | | | | (Found) | 64.50 | 5.44 | 5.98 |
| 9 | " | " | OC₂H₄OH | " | 173~176 | (Calc.) | 63.01 | 5.02 | 6.39 |
| | | | | | | (Found) | 62.90 | 5.11 | 6.28 |
| 10 | " | " | OCH₂COOC₂H₅ | " | 165~167 | (Calc.) | 62.50 | 5.00 | 5.83 |
| | | | | | | (Found) | 62.35 | 5.13 | 5.66 |
| 11 | " | " | NHC₄H₉ | " | 178~179 | (Calc.) | 66.82 | 6.01 | 9.35 |
| | | | | | | (Found) | 66.71 | 5.95 | 9.18 |
| 12 | " | " | N(C₄H₉)₂ | " | 143~145 | (Calc.) | 68.91 | 6.93 | 8.32 |
| | | | | | | (Found) | 68.88 | 7.05 | 8.22 |
| 13 | " | " | OCH₂CH=CH₂ | " | 190~192 | (Calc.) | 66.36 | 5.07 | 6.45 |
| | | | | | | (Found) | 66.19 | 5.01 | 6.54 |
| 14 | " | " | C₆H₅ | " | 218~219 | (Calc.) | 71.37 | 4.85 | 6.17 |
| | | | | | | (Found) | 71.50 | 4.92 | 6.30 |
| 15 | " | " | OC₂H₅ | 1H-benzimidazol-2-yl | 163~165 | (Calc.) | 68.15 | 5.43 | 10.37 |
| | | | | | | (Found) | 68.05 | 5.44 | 10.35 |
| 16 | " | " | OC₂H₄OH | " | 182~183 | (Calc.) | 65.56 | 5.23 | 9.98 |
| | | | | | | (Found) | 65.66 | 5.33 | 9.86 |
| 17 | " | " | OC₂H₄OC₂H₅ | " | 175~176 | (Calc.) | 66.82 | 5.79 | 9.35 |
| | | | | | | (Found) | 66.85 | 5.83 | 9.39 |
| 18 | " | " | OC₂H₄OC₂H₄OH | " | 153~154 | (Calc.) | 64.52 | 5.59 | 9.03 |
| | | | | | | (Found) | 64.55 | 5.60 | 9.00 |
| 19 | morpholino | | OC₄H₉ | 1H-benzimidazol-2-yl | 166~168 | (Calc.) | 67.11 | 5.37 | 9.40 |
| | | | | | | (Found) | 67.00 | 5.41 | 9.44 |
| 20 | piperidino | | " | " | 163~164 | (Calc.) | 70.11 | 5.84 | 9.44 |
| | | | | | | (Found) | 70.01 | 5.73 | 9.31 |

TABLE 1-continued

[Structure: coumarin with COX at 4-position, Y at 3-position, R1R2N- at 7-position]

| Example No. | R1 | R2 | X | Y | mp (°C.) | | Elemental analysis | | |
|---|---|---|---|---|---|---|---|---|---|
| | | | | | | | C | H | N |
| 21 | C2H5 | CH2CH=CH2 | OC2H5 | [N/S heterocycle] | 135~136 | (Calc.) | 62.50 | 5.21 | 7.29 |
| | | | | | | (Found) | 62.46 | 5.15 | 7.18 |
| 22 | " | " | " | COOC2H5 | 121~123 | (Calc.) | 64.34 | 6.17 | 3.75 |
| | | | | | | (Found) | 64.45 | 6.33 | 3.66 |
| 23 | " | C2H5 | OC4H9 | COOC4H9 | 128~129 | (Calc.) | 66.19 | 7.43 | 3.36 |
| | | | | | | (Found) | 66.21 | 7.27 | 3.37 |
| 24 | " | " | O-phenyl | benzoxazole | 215~218 | (Calc.) | 71.37 | 4.85 | 6.17 |
| | | | | | | (Found) | 71.33 | 4.82 | 6.15 |
| 25 | " | " | N(C4H9)2 | [N/O heterocycle] | 140~141 | (Calc.) | 68.34 | 7.52 | 9.57 |
| | | | | | | (Found) | 68.45 | 7.63 | 9.71 |
| 26 | " | " | OCH2COOC2H5 | [N/S heterocycle] | 148~150 | (Calc.) | 58.60 | 5.12 | 6.51 |
| | | | | | | (Found) | 58.55 | 5.10 | 6.43 |
| 27 | " | " | OH | benzothiazole | 260< | (Calc.) | 69.61 | 4.97 | 7.73 |
| | | | | | | (Found) | 69.51 | 5.05 | 7.62 |

What is claimed is:

1. A 4-carbonyl-substituted coumarin compound represented by the formula (I):

[Formula (I): coumarin with C(=O)X at 4-position, Y at 3-position, R3 on benzene ring, R1R2N- substituent]

wherein $R_1$ and $R_2$ are the same or a different group selected from an alkyl group having 2 to 6 carbon atoms and an alkenyl group having 3 carbon atoms,

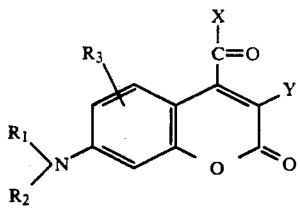

formed by bonding to each other; $R_3$ is a hydrogen atom, X is an alkoxy group having 1 to 6 carbon atoms, hydroxyl groups, phenyl group, aryloxy group having 6 to 12 carbon atoms, alkenyloxy group having 3 to 4 carbon atoms, aralkyloxy group having 7 to 8 carbon atoms, alkoxycarbonylalkoxy group having 7 to 8 carbon atoms, and a group represented by the following formula:

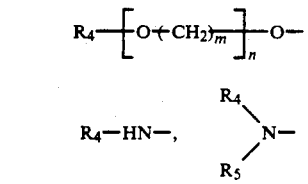

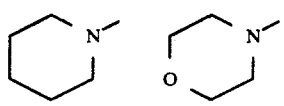

wherein $R_4$ and $R_5$ are selected from a hydrogen atom, alkyl group having 1 to 6 carbon atoms, m is an integer of 1, and n is an integer of from 1 to 2; and Y is alkoxycarbonyl group having 2 to 5 carbon atoms, or a heterocyclic ring represented by the following formula:

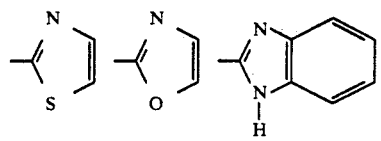

-continued

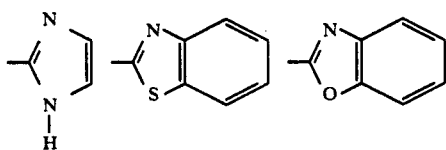

2. The 4-carbonyl substituted coumarin compound of claim 1 wherein X is selected from hydroxyl group, aryloxy group having 6 to 12 carbon atoms, aralkyloxy group having 7 to 8 carbon atoms, alkoxycarbonylalkoxy group having 7 to 8 carbon atoms, and a substituent represented by the formula:

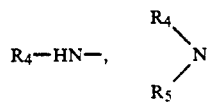

3. The 4-carbonyl-substituted coumarin compound of claim 1 wherein X is selected from alkoxy group having 1 to 6 carbon atoms, hydroxyl group, arloxy group having 6 to 12 carbon atoms, alkenyloxy group having 3 to 4 carbon atoms, aralkyloxy group having 7 to 8 carbon atoms, alkoxycarbonylalkoxy group having 7 to 8 carbon atoms, and a substituent represented by the formula:

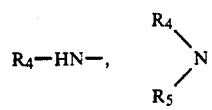

4. The 4-carbonyl-substituted coumarin compound of claim 3 wherein the heterocyclic ring is selected from:

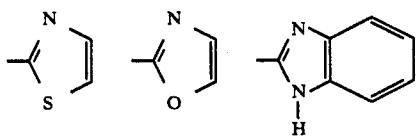

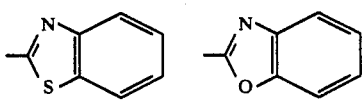

5. The 4-carbonyl-substituted coumarin compound of claim 2 wherein $R_1$ and $R_2$ are ethyl in formula (I).

6. The 4-carbonyl-substituted coumarin compound of claim 3 wherein $R_1$ and $R_2$ are ethyl in formula (I).

7. The 4-carbonyl-substituted coumarin compound of claim 4 wherein $R_1$ and $R_2$ are ethyl in formula (I).

* * * * *